United States Patent
Parrill-Baker et al.

(10) Patent No.: US 8,022,239 B2
(45) Date of Patent: Sep. 20, 2011

(54) MECHANISM-BASED INACTIVATORS OF AUTOTAXIN

(75) Inventors: Abby Louise Parrill-Baker, Memphis, TN (US); Daniel Lee Baker, Memphis, TN (US); Louis Edward Montedonico, Memphis, TN (US)

(73) Assignee: The University of Memphis Research Foundation, Memphis, TN (US)

( * ) Notice: Subject to any disclaimer, the term of this patent is extended or adjusted under 35 U.S.C. 154(b) by 0 days.

(21) Appl. No.: 12/572,921

(22) Filed: Oct. 2, 2009

(65) Prior Publication Data

US 2010/0136650 A1 Jun. 3, 2010

Related U.S. Application Data

(60) Provisional application No. 61/102,723, filed on Oct. 3, 2008.

(51) Int. Cl.
*C07F 9/147* (2006.01)
(52) U.S. Cl. ............................ 558/210; 558/89; 558/206
(58) Field of Classification Search .................. None
See application file for complete search history.

(56) References Cited

U.S. PATENT DOCUMENTS 3,989,825 A * 11/1976 Hogberg et al. ............... 514/120
5,714,361 A *  2/1998 Widlanski ..................... 435/184

OTHER PUBLICATIONS

Born et al, Journal of Biological Chemistry, vol. 270(43), pp. 25651-25655 (1995).*
Hata et al., JACS 91:16, pp. 4532-4535 (1969).*

* cited by examiner

*Primary Examiner* — Kamal Saeed
*Assistant Examiner* — Nyeemah A Grazier
(74) *Attorney, Agent, or Firm* — Wyatt, Tarrant & Combs, LLP; William S. Parks

(57) ABSTRACT

A novel class of compounds to inactivate autotaxin enzymes is provided. Such compounds include mono- and di-fluoromethylphenyl $C_{12}$-$C_{18}$ phosphodiesters and exhibit reactivity with autotaxin to ultimately reduce the size of the reactive sites thereon to prevent conversion of lysophosphatidyl choline to lysophophatidic acid. Furthermore, such compounds are non-cytotoxic, and can be incorporated within delivery forms for human ingestion. As such, these compounds accord an excellent manner of potentially reducing generation of certain cancers attributable to the presence of naturally occurring autotaxin within the human body. Methods of producing such novel compounds are encompassed within this invention as well as methods of inactivating autotaxin to certain degrees therewith.

7 Claims, No Drawings

MECHANISM-BASED INACTIVATORS OF AUTOTAXIN

CROSS-REFERENCE TO RELATED APPLICATIONS

This application claims priority to and the benefit of U.S. Provisional Patent Application No. 61/102,723, filed Oct. 3, 2008. This provisional application is hereby incorporated entirely by reference.

FIELD OF THE INVENTION

A novel class of compounds to inactivate autotaxin enzymes is provided. Such compounds include mono- and di-fluoromethylphenyl $C_{12}$-$C_{18}$ phosphodiesters and exhibit reactivity with autotaxin to ultimately reduce the size of the reactive sites thereon to prevent conversion of lysophosphatidyl choline to lysophosphatidic acid. Furthermore, such compounds can be incorporated within delivery forms for human ingestion. As such, these compounds afford an excellent manner of potentially reducing generation of certain cancers attributable to the presence of naturally occurring autotaxin within the human body. Methods of producing such novel compounds are encompassed within this invention as well as methods of inactivating autotaxin to certain degrees therewith.

BACKGROUND OF THE PRIOR ART

All U.S. patents cited within this specification are hereby incorporated by reference. Autotaxin, also known as ATX, ENPP2 or NPP2, short for Ectonucleotide pyrophosphatase phosphodiesterase 2 is an enzyme secreted within the human body. This molecule has been known for generating lysophosphatidic acid (LPA) through conversion of lysophosphatidyl choline (LPC) thereto via lysophospholipase D activity (the removal of choline from the base compound generates LPA). LPA has been realized to contribute to tumor cell growth, unfortunately, as the reactivity within the human body of LPA within certain tissues has resulted, in certain studies, of cancerous growths when present at certain levels. In this manner, then, it has been theorized that the greater the incidence of autotaxin activity within the human body, the greater the possibility of LPA generation. A reduction in the catalytic capabilities of autotaxin to convert the LPC molecule to LPA would theoretically permit an ultimate reduction in possibility of unwanted cell proliferation through reduced LPA presence within a subject's body.

The mechanism of autotaxin in terms of enzymatic activity and catalysis to form LPA resides in its phosphodiesterase capability. LPA can be generated from the cleavage of the phophodiester bonds of LPC, as well as its function as a phospholipase D enzyme (as presented in Formula I):

Formula I

LPC

ATX

LPA choline

In extracellular fluids, this enzymatic catalysis removes the choline group from LPC, leaving LPA, which has a tendency to stimulate cell growth and proliferation as well as chemotaxis. From this, it appears that the motility of tumor cells is increased as well, resulting in properties and gene expression within certain cancers (such as, for instance, breast cancer cells), causing further processing into a form that is bioactive and potentially dangerous. Metastasis and oncogenesis of cancer cells appear to occur as well with elevated levels of LPA present within a targeted region.

It has thus been determined that the ability to prevent, or at least reduce, the amount of LPA within human body holds great promise at, likewise, reducing, if not preventing, the onset of certain cancers. It has been theorized, as noted above, that autotaxin modifications may prevent the undesirable conversion from LPC to LPA; the ability to actually accomplish such a result has been elusive, however, at least to the degree necessary for effective broad-scale utilization of such a method. Any modification thereof must exhibit an ability to drastically reduce the activity of autotaxin while also proving to be non-cytotoxic, or, at least, not as cancer promoting as LPA itself.

Past work has been attempted at reducing activity of alkaline phosphatase enzymes, such as Myers and Widlanski (1993) *Mechanism-based Inactivation of Prostatic Acid Phosphatase*, Science, 262(5138):1451-1453, in terms of reacting 4-halomethylated aromatic phosphate esters therewith such molecules. Such has proven moderately successful, but has not contributed to any reduction in LPA generation as these prior studies were not directed at enzymes involved in LPA production, particularly in terms of LPC conversion thereto. Other suggested routes have been provided with regard to autotaxin inactivation, such as carbacyclic phosphatidic acid, as discussed in Baker, D. L. et al., (2006) *Carba Analogs of Cyclic Phosphatidic Acid Are Selective Inhibitors of Autotaxin and Cancer Invasion*, J. Biol. Chem. 281:22786-93, all to no avail, however, as these compounds exhibit no propensity to covalently modify autotaxin. Thus, the autotaxin modification reliability of such previously tested compounds has been rather low, unfortunately. Hence, to date, there exists a need to provide effective modifications to autotaxin enzymes for the reduction of LPC conversion to LPA readily and reliably. No such need has been met until now.

ADVANTAGES AND BRIEF DESCRIPTION OF THE INVENTION

It is thus an advantage of the present invention to provide reliable autotaxin inactivators for the purpose of reducing the conversion of LPC to LPA through the utilization of a readily available and easily produced compound (or compounds) that does not pose any significant known health risks. Another advantage is the ability for treatment with such compounds for cancer prevention treatment regimens.

Accordingly, this invention encompasses a compound conforming to the structure of Formula (II):

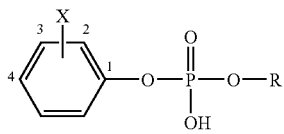

(II)

wherein R is $C_{12-18}$ alkyl or alkenyl; X is mono- or difluoromethyl($CH_2F$ or $CHF_2$); and X is in either the 2 or 4 position (ortho- or para-substitution, in essence). For purposes of this disclosure, as it pertains to the R groups potentially present on the Formula II compound, the notation of 18:0 means octadecyl, 16:0 is hexadecyl, 14:0 is tetradecyl, 12:0 is dodecyl, and any notation with the number 1 includes (such as 16:1) indicates alkenyl, with the double bond present anywhere within the carbon chain.

As well, this invention encompasses the utilization of a compound including a phosphodiester and either a monofluoromethylphenyl or difluoromethylphenyl group, preferably a compound as defined within the structure of Formula (II), above, to effectuate a reduction in activity of autotaxin in terms of potential conversion of LPC to LPA, particularly through structural modifications to prevent interaction of the LPC compound within the active site of the modified autotaxin enzyme. A method of producing such compounds is also encompassed within this invention, comprising the sequential steps of:

a) reacting phosphorus oxychloride with a fatty alcohol;

b) reacting the resultant compound of step "a" with a hydroxybenzaldehyde, thereby forming a phosphodiester compound;

c) reacting said phosphodiester compound with a cyanoethanol to form a phosphotriester compound;

d) reacting said phosphotriester compound with bis(2-methoxyethyl)-sulfur trifluoride, wherein said reaction with bis(2-methoxyethyl)-sulfur trifluoride is optionally preceded by reducing said phosphotriester compound with sodium borohydride, thereby producing a fluorinated compound; and e) deprotecting the resultant fluorinated compound of step "d". Such a novel method is described in greater detail below.

DETAILED DESCRIPTION OF THE INVENTION AND PREFERRED EMBODIMENTS

Basically, it has been realized that such compounds as listed above (di- and mono-fluoromethylphenyl $C_{10}$-$C_{18}$ phosphodiesters) exhibit excellent capability of reducing the activity of autotaxin such that the potential conversion of LPC to LPA thereby is compromised. The following scheme shows the general reaction leading to inactivation of the autotaxin enzyme through the utilization of the inventive compounds noted above:

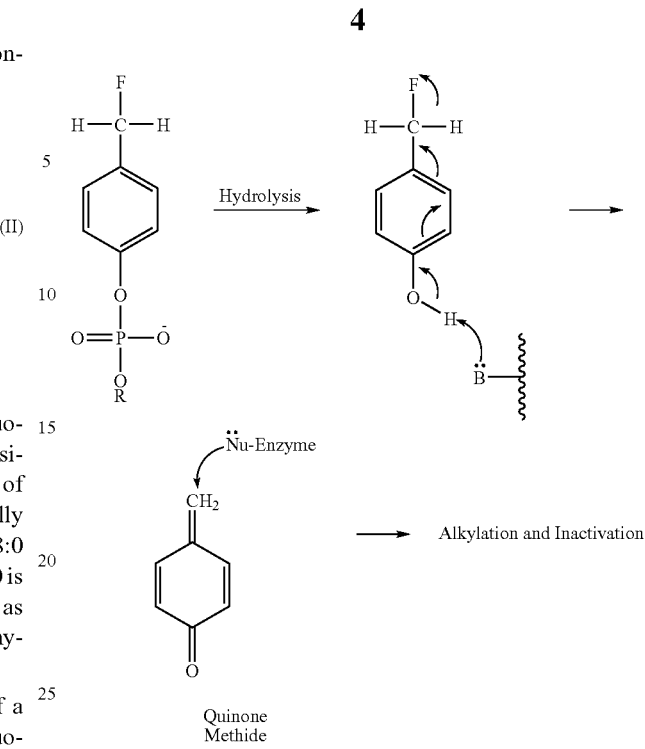

The figure above shows how the mechanism-based inhibitors participate in the enzyme-catalyzed reaction to generate a reactive species that irreversibly inactivates the enzyme. The first step of the enzyme-catalyzed reaction is attack of the catalytic threonine upon the phosphate group of the substrate. Within the fluoro (or difluoro) methylphenyl leaving group, a fluoride ion is ejected, generating the reactive quinone methide. In the second step, the quinone methide reacts with an unknown nucleophilic amino acid sidechain (such as lysine, arginine, histidine, aspartate, glutamate, serine, threonine or cysteine). The irreversible modification of the active site prevents other substrate molecules from fitting into the reduced space remaining after modification, thus preventing generation of LPA from the natural substrate, LPC.

In this manner, there is a strong possibility that such compounds may prove highly effective at reducing the chances of a target subject incurring cancerous growths typically due to the presence of LPA in their systems.

The preferred compounds for this autotaxin inactivation function are those that conform to the structure of Formula (II), noted above. Preferably, though, the alkyl chain is 14 or 16 carbons in length, with either the di- or mono-fluoromethylphenyl group present. If the chain is 18 carbons in length, then it is preferable, though not required, for the pendant group to be $CFH_2$. Such specific compounds have been found to provide the most effective autotaxin inactivation capability results and thus the greatest promise in terms of effective cancer prevention treatments.

These compounds may be included in a composition of any type that is introduced within a patient's body intravenously, and, if possible, through ingestion.

In terms of the form such compositions may take, any orally ingestible form is possible. This list includes, without limitation, liquids, liquid capsules, tablets, coated tablets, minitablets, capsules with individual beads, and the like. If in coated tablet form, such compositions may be of sustained release type, and may include a water insoluble but permeable film coating surrounding a core tablet and a particulate, water-soluble, pore-forming material dispersed within the film coating. Such a system thus provides an osmotic gradient and channel forming system. Typical coatings have included carnauba wax, cysteine hydrochloride, hydroxypropyl methylcellulose, magnesium stearate, microcrystalline cellulose, polyethylene glycol and titanium dioxide. Other therapeutic agents may be included with these anticancer agents as well, as long as neither interferes with the effectiveness of the other in the user's body.

The general method of production of the inventive compounds involves an initial generation of benzaldehyde phosphodiester through the reaction of phosphorous oxychloride with a long chain alcohol ($C_{10}$-$C_{18}$), and subsequently with p-hydroxybenzaldehyde, and lastly with water. This initial precursor reacts with cyanoethanol in the presence of dicyclohexyl carbodiimide (DCC) and dimethyl aminopyridine (DMAP) to generate a phosphotriester, needed for the subsequent fluorination of the intermediary compound. Such a two-step process has proved to be excellent at permitting a simplified purification procedure for the production of the intermediary cyanoethanol-protected diester compound, thereby permitting more effective triester formation for easy fluorination thereof. Such fluorination is generally accomplished through the reaction of either bis(2-methoxyethyl)-sulfur trifluoride (e.g., DEOXO-FLUOR™ from Air Products and Chemicals, Inc.) to create the difluoromethyl compound, or through the initial reduction with sodium borohydride with subsequent fluorination with Deoxofluor to generate the monofluoromethyl compound. The general reaction scheme is:

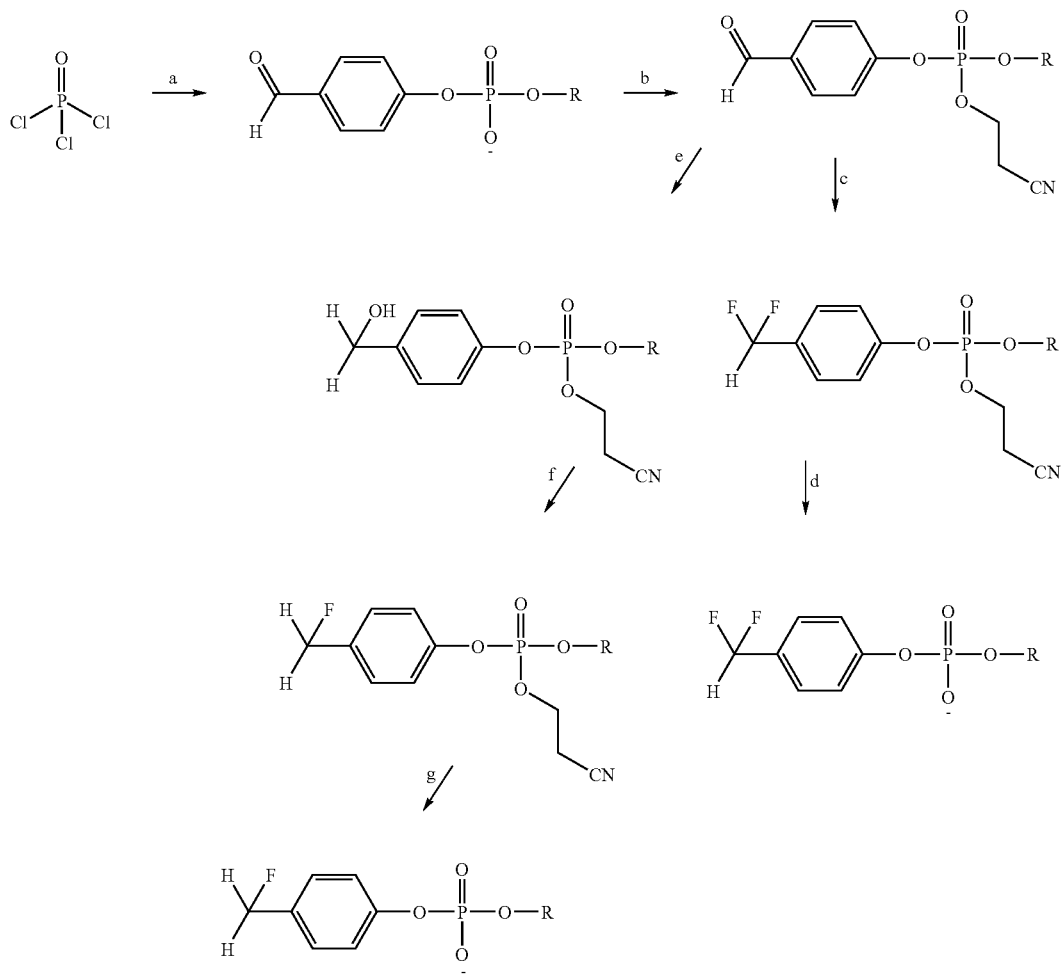

(a) 4-hydroxybenzaldehyde, R—OH, THF, 1 hr (b) DCC, DMAP, cyanoethanol, $CH_2Cl_2$, $H_2O$, 3 days (c) Deoxofluor, ethanol, $CH_2Cl_2$, 16 hrs (d) n-propylamine, pyridine, 10 min. (e) $NaBH_4$, $H_2O$, THF, 20 min. (f) Deoxofluor, $CH_2Cl_2$, 12 hrs (g) n-propylamine, pyridine, 10 min.
(with further confirmation of compound structures through mass spectrometric and nuclear magnetic resonance spectroscopic analysis).

In terms of reacting these novel compounds with autotaxin, they react upon mixing with autotaxin in aqueous solutions such as assay buffer or blood. The measured inhibition should increase upon preincubation time (inhibitor plus enzyme alone) prior to addition of substrate, thereby indicating the reduction of ability of the autotaxin to modify the substrate (such as LPC) to the undesired compound (such as LPA).

The specific compounds below, as well as the following exemplified methods of producing such and methods of using such compounds are non-limiting in nature and are thus indicative of the preferred embodiments of this invention.

PREFERRED EMBODIMENTS OF THE INVENTION

Compound Production

The specific compounds were produced as noted below, in the following non-limiting examples:

Example 1

(18:0)-p-difluorophosphodiester

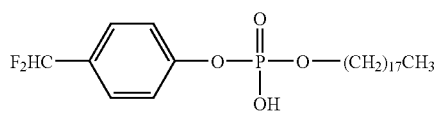

Phosphorous oxychloride (1 eq.) was added to a round bottom flask and dissolved in tetrahydrofuran (THF). The round bottom flask was then placed in an ice bath to maintain a 0° C. temperature. Octadecanol (1 eq.) dissolved in THF with triethylamine (TEA) (1 eq.) was added dropwise to the phosphorous oxychloride/THF solution. Once all of the octadecanol/THF/TEA solution was added (~20 min.), the reaction mixture was stirred for an additional 40 minutes at 0° C. A solution of p-hydroxybenzaldehyde (1 eq.) in THF with TEA (1 eq.) was added dropwise to the reaction flask and was stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. After an extraction with chloroform/methanol/water 1:1.5:1 (v/v/v), the (18:0)-p-phosphodiester was dissolved in 40% ethyl acetate/hexane and centrifuged for 7 minutes. The supernatant was decanted and the insoluble fractions were combined.

The relatively pure (18:0)-p-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (18:0)-p-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.) was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (18:0)-p-phosphodiester was split into two roughly equal portions. The first portion was used for direct fluorination and the second portion was used for reduction followed by fluorination (Example 2). Protected (18:0)-p-phosphodiester (1 eq.) was dried over phosphorous pentoxide for 12 hours and dissolved in dichloromethane. The reaction flask was sealed and placed in an ice bath to maintain 0° C. temperature. Deoxofluor (2 eq.) in dichloromethane was slowly added (~2 minutes) and ethanol (0.2 eq.) was added to generate a catalyst, HF. The ice bath was removed and the reaction mixture was stirred for 16 hours. An extraction with dichloromethane/saturated sodium bicarbonate solution 1:1 (v/v) was performed and the organic layer was collected.

After drying in vacuo, the protected (18:0)-p-difluorophosphodiester was purified by flash column chromatography using 40% ethyl acetate/hexane then switching to 80% ethyl acetate/hexane for a step gradient elution. For deprotection, the protected (18:0)-p-difluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (18:0)-p-difluoro-phosphodiester. An extraction with chloroform/methanol/brine 1:1.5:1 was performed to generate the sodium salt of the (18:0)-p-difluorophosphodiester.

Example 2

(18:0)-p-monofluorophosphodiester

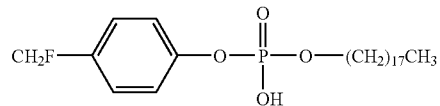

Phosphorous oxychloride (1 eq.) was added to a round bottom flask and dissolved in tetrahydrofuran (THF). The round bottom flask was then placed in an ice bath to maintain a 0° C. temperature. Octadecanol (1 eq.) dissolved in THF with triethylamine (TEA) (1 eq.) was added dropwise to the phosphorous oxychloride/THF solution. Once all of the octadecanol/THF/TEA solution was added (~20 min.), the reaction mixture was stirred for an additional 40 minutes at 0° C. A solution of p-hydroxybenzaldehyde (1 eq.) in THF with TEA (1 eq.) was added dropwise to the reaction flask and was stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. After an extraction with chloroform/methanol/water 1:1.5:1 (v/v/v), the (18:0)-p-phosphodiester was dissolved in 40% ethyl acetate/hexane and centrifuged for 7 minutes. The supernatant was decanted and the insoluble fractions were combined.

The relatively pure (18:0)-p-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (18:0)-p-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.)

was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (18:0)-p-phosphodiester was split into two roughly equal portions. The first portion was used for direct fluorination (Example 1) and the second portion was used for reduction followed by fluorination. For reduction, the protected (18:0)-p-phosphodiester (1 eq.) was dissolved in THF/water 3:0.1 equivalents respectively and sodium borohydride (1 eq.) was added to the reaction flask. The reaction mixture was stirred until all sodium borohydride dissolved (~2 minutes) and continued stirring for an additional 10 minutes. Water (3 eq.) was added and the reaction mixture was stirred an additional 10 minutes. All solvents were removed in vacuo and the reduced, protected (18:0)-p-phosphodiester was purified by flash column chromatography using 40% ethyl acetate/hexane then switching to 80% ethyl acetate/hexane for a step gradient elution. The reduced, protected (18:0)-p-phosphodiester (1 eq.) was dried over phosphorous pentoxide for 12 hours and dissolved in dichloromethane. The reaction flask was sealed and placed in an ice bath to maintain 0° C. temperature. Deoxofluor (2 eq.) in dichloromethane was slowly added (~2 minutes). The ice bath was removed and the reaction mixture was stirred for 12 hours. An extraction with dichloromethane/saturated sodium bicarbonate solution 1:1 (v/v) was performed and the organic layer was collected.

After drying in vacuo, the protected (18:0)-p-monofluorophosphodiester was purified by flash column chromatography using 40% ethyl acetate/hexane then switching to 80% ethyl acetate/hexane for a step gradient elution. For deprotection, the protected (18:0)-p-monofluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (18:0)-p-monofluoro-phosphodiester. An extraction with chloroform/methanol/brine 1:1.5:1 (v/v/v) was performed to generate the sodium salt of the (18:0)-p-monofluorophosphodiester.

Example 3

(16:0)-p-difluorophosphodiester

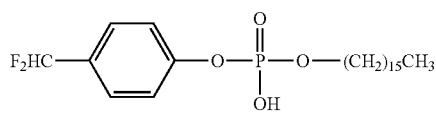

Phosphorous oxychloride (1 eq.) was added to a round bottom flask and dissolved in tetrahydrofuran (THF). The round bottom flask was then placed in an ice bath to maintain a 0° C. temperature. Hexadecanol (1 eq.) dissolved in THF with triethylamine (TEA) (1 eq.) was added dropwise to the phosphorous oxychloride/THF solution. Once all of the hexadecanol/THF/TEA solution was added (~20 minutes), the reaction mixture was stirred for an additional 40 minutes at 0° C. A solution of p-hydroxybenzaldehyde (1 eq.) in THF with TEA (1 eq.) was added dropwise to the reaction flask and was stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. After an extraction with chloroform/methanol/water 1:1.5:1 (v/v/v), the (16:0)-p-phosphodiester was dissolved in 40% ethyl acetate/hexane and centrifuged for 7 minutes. The supernatant was decanted and the insoluble fractions were combined.

The relatively pure (16:0)-p-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (16:0)-p-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.) was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (16:0)-p-phosphodiester was split into two roughly equal portions. The first portion was used for direct fluorination and the second portion was used for (Example 4) reduction followed by fluorination. Protected (16:0)-p-phosphodiester (1 eq.) was dried over phosphorous pentoxide for 12 hours and dissolved in dichloromethane. The reaction flask was sealed and placed in an ice bath to maintain 0° C. temperature. Deoxofluor (2 eq.) in dichloromethane was slowly added (~2 minutes) and ethanol (0.2 eq.) was added to generate a catalyst, HF. The ice bath was removed and the reaction mixture was stirred for 16 hours. An extraction with dichloromethane/saturated sodium bicarbonate solution 1:1 (v/v) was performed and the organic layer was collected.

After drying in vacuo, the protected (16:0)-p-difluorophosphodiester was purified by flash column chromatography using 40% ethyl acetate/hexane then switching to 80% ethyl acetate/hexane for a step gradient elution. For deprotection, the protected (16:0)-p-difluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (16:0)-p-difluorophosphodiester. An extraction with chloroform/methanol/brine 1:1.5:1 (v/v/v) was performed to generate the sodium salt of the (16:0)-p-difluorophosphodiester.

Example 4

(16:0)-p-monofluorophosphodiester

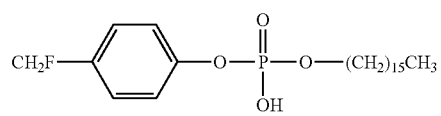

Phosphorous oxychloride (1 eq.) was added to a round bottom flask and dissolved in tetrahydrofuran (THF). The round bottom flask was then placed in an ice bath to maintain a 0° C. temperature. Hexadecanol (1 eq.) dissolved in THF with triethylamine (TEA) (1 eq.) was added dropwise to the phosphorous oxychloride/THF solution. Once all of the hexadecanol/THF/TEA solution was added (~20 minutes), the reaction mixture was stirred for an additional 40 minutes at 0° C. A solution of p-hydroxybenzaldehyde (1 eq.) in THF with TEA (1 eq.) was added dropwise to the reaction flask and stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. After an extraction with chloroform/methanol/water 1:1.5:1 (v/v/v), the (16:0)-p-phosphodiester was dissolved in 40% ethyl acetate/hexane and centrifuged for 7 minutes. The supernatant was decanted and the insoluble fractions were combined.

The relatively pure (16:0)-p-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (16:0)-p-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.) was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (16:0)-p-phosphodiester was split into two roughly equal portions. The first portion was used for direct fluorination (Example 3) and the second portion was used for reduction followed by fluorination. For reduction, the protected (16:0)-p-phosphodiester (1 eq.) was dissolved in THF/water 3:0.1 equivalents respectively and sodium borohydride (1 eq.) was added to the reaction flask. The reaction mixture was stirred until all sodium borohydride dissolved (~2 minutes) and continued stirring for an additional 10 minutes. Water (3 eq.) was added and the reaction mixture was stirred an additional 10 minutes. All solvents were removed in vacuo and the reduced, protected (16:0)-p-phosphodiester was purified by flash column chromatography using 40% ethyl acetate/hexane then switching to 80% ethyl acetate/hexane for a step gradient elution.

The reduced, protected (16:0)-p-phosphodiester (1 eq.) was dried over phosphorous pentoxide for 2 hours and dissolved in dichloromethane. The reaction flask was sealed and placed in an ice bath to maintain 0° C. temperature. Deoxofluor (2 eq.) in dichloromethane was slowly added (~2 minutes). The ice bath was removed and the reaction mixture was stirred for 12 hours. An extraction with dichloromethane/saturated sodium bicarbonate solution 1:1 (v/v) was performed and the organic layer was collected.

After drying in vacuo, the protected (16:0)-p-monofluorophosphodiester was purified by flash column chromatography using 40% ethyl acetate/hexane then switching to 80% ethyl acetate/hexane for a step gradient elution. For deprotection, the protected (16:0)-p-monofluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (16:0)-p-monofluoro-phosphodiester. An extraction with chloroform/methanol/brine 1:1.5:1 (v/v/v) was performed to generate the sodium salt of the (16:0)-p-monofluorophosphodiester.

Example 5

(14:0)-p-difluorophosphodiester

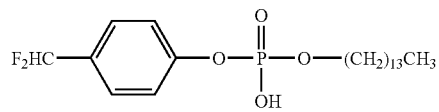

Phosphorous oxychloride (1 eq.) was added to a round bottom flask and dissolved in tetrahydrofuran (THF). The round bottom flask was then placed in an ice bath to maintain a 0° C. temperature. Tetradecanol (1 eq.) dissolved in THF with triethylamine (TEA) (1 eq.) was added dropwise to the phosphorous oxychloride/THF solution. Once all of the tetradecanol/THF/TEA solution was added (~20 minutes), the reaction mixture was stirred for an additional 40 minutes at 0° C. A solution of p-hydroxybenzaldehyde (1 eq.) in THF with TEA (1 eq.) was added dropwise to the reaction flask and was stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. After an extraction with chloroform/methanol/water 1:1.5:1 (v/v/v), the (14:0)-p-phosphodiester was dissolved in 40% ethyl acetate/hexane and centrifuged for 7 minutes. The supernatant was decanted and the insoluble fractions were combined.

The relatively pure (14:0)-p-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (14:0)-p-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.) was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (14:0)-p-phosphodiester was split into two roughly equal portions. The first portion was used for direct fluorination and the second portion was used for reduction followed by fluorination (Example 6). Protected (14:0)-p-phosphodiester (1 eq.) was dried over phosphorous pentoxide for 12 hours and dissolved in dichloromethane. The reaction flask was sealed and placed in an ice bath to maintain 0° C. temperature. Deoxofluor (2 eq.) in dichloromethane was slowly added (~2 minutes) and ethanol (0.2 eq.) was added to generate a catalyst, HF. The ice bath was removed and the reaction mixture was stirred for 16 hours. An extraction with dichloromethane/saturated sodium bicarbonate solution 1:1 (v/v) was performed and the organic layer was collected.

After drying in vacuo, the protected (14:0)-p-difluorophosphodiester was purified by flash column chromatography using 40% ethyl acetate/hexane then switching to 80% ethyl acetate/hexane for a step gradient elution. For deprotection, the protected (14:0)-p-difluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (14:0)-p-difluorophosphodiester. An extraction with chloroform/methanol/brine 1:1.5:1 (v/v/v) performed to generate the sodium salt of the (14:0)-p-difluorophosphodiester.

Example 6

(14:0)-p-monofluorophosphodiester

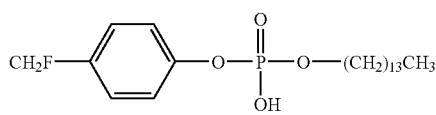

Phosphorous oxychloride (1 eq.) was added to a round bottom flask and dissolved in tetrahydrofuran (THF). The round bottom flask was then placed in an ice bath to maintain a 0° C. temperature. Tetradecanol (1 eq.) dissolved in THF with triethylamine (TEA) (1 eq.) was added dropwise to the phosphorous oxychloride/THF solution. Once all of the tetradecanol/THF/TEA solution was added (~20 minutes), the reaction mixture was stirred for an additional 40 minutes at 0° C. A solution of p-hydroxybenzaldehyde (1 eq.) in THF with TEA (1 eq.) was added dropwise to the reaction flask and was stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. After an extraction with chloroform/methanol/water 1:1.5:1 (v/v/v), the (14:0)-p-phosphodiester was dissolved in 40% ethyl acetate/hexane and centrifuged for 7 minutes. The supernatant was decanted and the insoluble fractions were combined.

The relatively pure (14:0)-p-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (14:0)-p-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.) was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (14:0)-p-phosphodiester was split into two roughly equal portions. The first portion was used for direct fluorination (Example 5) and the second portion was used for reduction followed by fluorination. For reduction, the protected (14:0)-p-phosphodiester (1 eq.) was dissolved in THF/water 3:0.1 (v/v) respectively and sodium borohydride (1 eq.) was added to the reaction flask. The reaction mixture was stirred until all sodium borohydride dissolved (~2 minutes) and continued stirring for an additional 10 minutes. Water (3 eq.) was added and the reaction mixture was stirred an additional 10 minutes. All solvents were removed in vacuo and the reduced, protected (14:0)-p-phosphodiester was purified by flash column chromatography using 40% ethyl acetate/hexane then switching to 80% ethyl acetate/hexane for a step gradient elution.

The reduced, protected (14:0)-p-phosphodiester (1 eq.) was dried over phosphorous pentoxide for 12 hours and dissolved in dichloromethane. The reaction flask was sealed and placed in an ice bath to maintain 0° C. temperature. Deoxofluor (2 eq.) in dichloromethane was slowly added (~2 minutes). The ice bath was removed and the reaction mixture was stirred for 12 hours. An extraction with dichloromethane/saturated sodium bicarbonate solution 1:1 (v/v) was performed and the organic layer was collected.

After drying in vacuo, the protected (14:0)-p-monofluorophosphodiester was purified by flash column chromatography using 40% ethyl acetate/hexane then switching to 80% ethyl acetate/hexane for a step gradient elution. For deprotection, the protected (14:0)-p-monofluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (14:0)-p-monofluoro-phosphodiester. An extraction with chloroform/methanol/brine 1:1.5:1 (v/v/v) was performed to generate the sodium salt of the (14:0)-p-monofluorophosphodiester.

Example 7

(12:0)-p-difluorophosphodiester

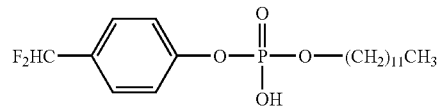

Phosphorous oxychloride (1 eq.) was added to a round bottom flask and dissolved in tetrahydrofuran (THF). The round bottom flask was then placed in an ice bath to maintain a 0° C. temperature. Dodecanol (1 eq.) dissolved in THF with triethylamine (TEA) (1 eq.) was added dropwise to the phosphorous oxychloride/THF solution. Once all of the dodecanol/THF/TEA solution was added (~20 minutes), the reaction mixture was stirred for an additional 40 minutes at 0° C. A solution of p-hydroxybenzaldehyde (1 eq.) in THF with TEA (1 eq.) was added dropwise to the reaction flask and was stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. After an extraction with chloroform/methanol/water 1:1.5:1 (v/v/v), the (12:0)-p-phosphodiester was dissolved in 40% ethyl acetate/hexane and centrifuged for 7 minutes. The supernatant was decanted and the insoluble fractions were combined.

The relatively pure (12:0)-p-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (12:0)-p-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.) was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (12:0)-p-phosphodiester was split into two roughly equal portions. The first portion was used for direct fluorination and the second portion was used for reduction followed by fluorination (Example 8). Protected (12:0)-p-phosphodiester (1 eq.) was dried over phosphorous pentoxide for 12 hours and dissolved in dichloromethane. The reaction flask was sealed and placed in an ice bath to maintain 0° C. temperature. Deoxofluor (2 eq.) in dichloromethane was slowly added (~2 minutes) and ethanol (0.2 eq.) was added to generate a catalyst, HF. The ice bath was removed and the reaction mixture was stirred for 16 hours. An extraction with dichloromethane/saturated sodium bicarbonate solution 1:1 (v/v) was performed and the organic layer was collected.

After drying in vacuo, the protected (12:0)-p-difluorophosphodiester was purified by flash column chromatography using 40% ethyl acetate/hexane then switching to 80% ethyl acetate/hexane for a step gradient elution. For deprotection, the protected (12:0)-p-difluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (12:0)-p-difluorophosphodiester. An extraction with chloroform/methanol/brine 1:1.5:1 (v/v/v) was performed to generate the sodium salt of the (12:0)-p-difluorophosphodiester.

Example 8

(12:0)-p-monofluorophosphodiester

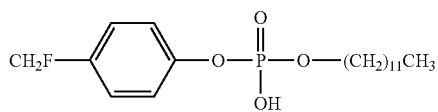

Phosphorous oxychloride (1 eq.) was added to a round bottom flask and dissolved in tetrahydrofuran (THF). The round bottom flask was then placed in an ice bath to maintain a 0° C. temperature. Dodecanol (1 eq.) dissolved in THF with triethylamine (TEA) (1 eq.) was added dropwise to the phosphorous oxychloride/THF solution. Once all of the dodecanol/THF/TEA solution was added (~20 minutes), the reaction mixture was stirred for an additional 40 minutes at 0° C. A solution of p-hydroxybenzaldehyde (1 eq.) in THF with TEA (1 eq.) was added dropwise to the reaction flask and was stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. After an extraction with chloroform/methanol/water 1:1.5:1 (v/v/v), the (14:0)-p-phosphodiester was dissolved in 40% ethyl acetate/hexane and centrifuged for 7 minutes. The supernatant was decanted and the insoluble fractions were combined.

The relatively pure (12:0)-p-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (12:0)-p-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.) was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (12:0)-p-phosphodiester was split into two roughly equal portions. The first portion was used for direct fluorination (Example 7) and the second portion was used for reduction followed by fluorination. For reduction, the protected (12:0)-p-phosphodiester (1 eq.) was dissolved in THF/water 3:0.1 equivalents respectively and sodium borohydride (1 eq.) was added to the reaction flask. The reaction mixture was stirred until all sodium borohydride dissolved (~2 minutes) and continued stirring for an additional 10 minutes. Water (3 eq.) was added and the reaction mixture was stirred an additional 10 minutes. All solvents were removed in vacuo and the reduced, protected (12:0)-p-phosphodiester was purified by flash column chromatography using 40% ethyl acetate/hexane then switching to 80% ethyl acetate/hexane for a step gradient elution.

The reduced, protected (12:0)-p-phosphodiester (1 eq.) was dried over phosphorous pentoxide for 12 hours and dissolved in dichloromethane. The reaction flask was sealed and placed in an ice bath to maintain 0° C. temperature. Deoxofluor (2 eq.) in dichloromethane was slowly added (~2 minutes). The ice bath was removed and the reaction mixture was stirred for 12 hours. An extraction with dichloromethane/saturated sodium bicarbonate solution 1:1 (v/v) was performed and the organic layer was collected.

After drying in vacuo, the protected (12:0)-p-monofluorophosphodiester was purified by flash column chromatography using 40% ethyl acetate/hexane then switching to 80% ethyl acetate/hexane for a step gradient elution. For deprotection, the protected (12:0)-p-monofluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (12:0)-p-monofluoro-phosphodiester. An extraction with chloroform/methanol/brine 1:1.5:1 (v/v/v) was performed to generate the sodium salt of the (12:0)-p-monofluorophosphodiester.

Example 9

(16:0)-o-difluorophosphodiester

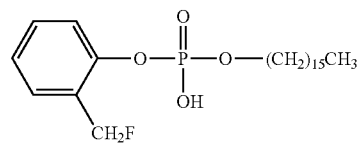

Phosphorous oxychloride (1 eq.) was added to a round bottom flask and dissolved in tetrahydrofuran (THF). The round bottom flask was then placed in an ice bath to maintain a 0° C. temperature. Hexadecanol (1 eq.) dissolved in THF with triethylamine (TEA) (1 eq.) was added dropwise to the phosphorous oxychloride/THF solution. Once all of the hexadecanol/THF/TEA solution was added (~20 min.), the reaction mixture was stirred for an additional 40 minutes at 0° C. A solution of o-hydroxybenzaldehyde (1 eq.) in THF was added dropwise to the reaction flask followed by TEA (1 eq.) in THF. The reaction mixture was stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. An extraction with chloroform/methanol/water 1:1.5:1 (v/v/v) respectively was performed and the (16:0)-o-phosphodiester was used without further purification.

The relatively pure (16:0)-o-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (16:0)-o-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.) was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (16:0)-o-phosphodiester was split into two roughly equal portions. The first portion was used for direct fluorination and the second portion was used for reduction followed by fluorination (Example 10). Protected (16:0)-o-phosphodiester (1 eq.) was dried over phosphorous pentoxide for 12 hours and dissolved in dichloromethane. The reaction flask was sealed and placed in an ice bath to maintain 0° C. temperature. Deoxofluor (2 eq.) in dichloromethane was slowly added (~2 minutes) and ethanol (0.2 eq.) was added to generate a catalyst, HF. The ice bath was removed and the reaction mixture was stirred for 16 hours. An extraction with dichloromethane/saturated sodium bicarbonate solution 1:1 (v/v) was performed and the organic layer was collected.

After drying in vacuo, the protected (16:0)-o-difluorophosphodiester was purified by flash column chromatography using 40% ethyl acetate/hexane then switching to 80% ethyl acetate/hexane for a step gradient elution. For deprotection, the protected (16:0)-o-difluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (16:0)-o-difluorophosphodiester. An extraction with chloroform/methanol/brine 1:1.5:1 (v/v/v) was performed to generate the sodium salt of the (16:0)-o-difluorophosphodiester.

Example 10

(16:0)-o-monofluorophosphodiester

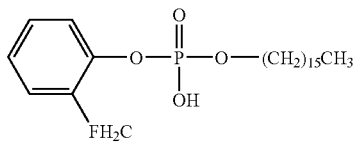

Phosphorous oxychloride (1 eq.) was added to a round bottom flask and dissolved in tetrahydrofuran (THF). The round bottom flask was then placed in an ice bath to maintain a 0° C. temperature. Hexadecanol (1 eq.) dissolved in THF with triethylamine (TEA) (1 eq.) was added dropwise to the phosphorous oxychloride/THF solution. Once all of the hexadecanol/THF/TEA solution was added (~20 min.), the reaction mixture was stirred for an additional 40 minutes at 0° C. A solution of o-hydroxybenzaldehyde (1 eq.) in THF was added dropwise to the reaction flask followed by TEA (1 eq.) in THF. The reaction mixture was stirred for an additional 40 minutes at 0° C. Water (1 eq.) and TEA (1 eq.) were added to the reaction mixture which was allowed to stir for 60 minutes at 0° C. The contents of the reaction flask were then vacuum filtered and dried in vacuo. An extraction with chloroform/methanol/water 1:1.5:1 (v/v/v) respectively was performed and the (16:0)-o-phosphodiester was used without further purification.

The relatively pure (16:0)-o-phosphodiester (1 eq.), DCC (2.2 eq.) and DMAP (0.1 eq.) were dried over phosphorous pentoxide for 12 hours. Cyanoethanol (1.1 eq.) was dissolved in dichloromethane and dried with magnesium sulfate for 12 hours. The (16:0)-o-phosphodiester was dissolved in dichloromethane and DCC and DMAP were added to the reaction flask. The flask was sealed with a septum and purged with nitrogen after adding the cyanoethanol solution. The reaction was stirred for 48 hours at room temperature. Water (5 eq.) was added and the reaction mixture was stirred for an additional 24 hours. The contents of the reaction flask were vacuum filtered and dried in vacuo. After an extraction with chloroform/brine 1:1 (v/v), the coupled product was purified by flash column chromatography using 40% ethyl acetate/hexane then switching to 80% ethyl acetate/hexane for a step gradient elution.

After purification, the protected (16:0)-o-phosphodiester was split into two roughly equal portions. The first portion was used for direct fluorination (Example 9) and the second portion was used for reduction followed by fluorination. For reduction, the protected (16:0)-o-phosphodiester (1 eq.) was dissolved in THF/water 3:0.1 equivalents respectively and sodium borohydride (1 eq.) was added to the reaction flask. The reaction mixture was stirred until all sodium borohydride dissolved (~2 minutes) and continued stirring for an additional 10 minutes. Water (3 eq.) was added and the reaction mixture was stirred an additional 10 minutes. All solvents were removed in vacuo and the reduced, protected (16:0)-o-phosphodiester was purified by flash column chromatography using 40% ethyl acetate/hexane then switching to 80% ethyl acetate/hexane for a step gradient elution. The reduced, protected (16:0)-o-phosphodiester (1 eq.) was dried over phosphorous pentoxide for 12 hours and dissolved in dichloromethane. The reaction flask was sealed and placed in an ice bath to maintain 0° C. temperature. Deoxofluor (2 eq.) in dichloromethane was slowly added (~2 minutes). The ice bath was removed and the reaction mixture was stirred for 12 hours. An extraction with dichloromethane/saturated sodium bicarbonate solution 1:1 (v/v) was performed and the organic layer was collected.

After drying in vacuo, the protected (16:0)-o-monofluoro-phosphodiester was purified by flash column chromatography using 40% ethyl acetate/hexane then switching to 80% ethyl acetate/hexane for a step gradient elution. For deprotection, the protected (16:0)-o-monofluoro-phosphodiester (1 eq.) was dissolved in pyridine. N-propylamine (100 eq.) in pyridine was added to the reaction flask and the clear solution was stirred for 10 minutes at room temperature. All solvents were removed in vacuo to yield the n-propylammonium salt of the (16:0)-o-monofluoro-phosphodiester. An extraction with chloroform/methanol/brine (v/v/v) was performed to generate the sodium salt of the (16:0)-o-monofluorophos-phodiester.

These compounds were then introduced into an aqueous solution for reaction with autotaxin.

Autotaxin Inactivation Analysis

The efficacy of these compounds was determined by evaluating autotaxin-mediated hydrolysis of the synthetic LPC analog FS3 at specific excitation and emission wavelengths resulting from cleavage of FS-3 by autotaxin. The test protocol was as follows:

MDA-MB-435 cells were cultured at 37° C. and 5% $CO_2$ in Dulbecco's Modified Eagle Medium (DMEM) (MediaTech, Herndon, Va.) containing 5% fetal bovine serum (Hyclone, Logan, Utah), 100 U/ml penicillin, 100 μg/ml streptomycin (Hyclone, Logan, Utah) and 292 μg/ml L-glutamine (Hyclone, Logan, Utah). Cells were grown to ~80% confluence at which time the cells were washed twice with sterile phosphate buffered saline prior to the addition of serum free DMEM containing L-glutamine. Conditioned medium was collected after 24-30 hours, supplemented with 20% ethylene glycol and was clarified by centrifugation at 3000×g and 4° C. for 10 min. The media was concentrated ~10 fold and buffer exchanged into Tris (50 mM, pH 7.4) containing 20% ethylene glycol using an Amicon 8050 cell fitted with a PM30 filter (MILLIPORE®, Billerica, Mass.). Aliquots of concentrated conditioned media were stored at 4° C. until needed.

ATX inhibition was assayed using FS-3 (Echelon Biosciences, Inc., Salt Lake City, Utah, USA) as a substrate and ~10 times concentrated conditioned serum-free medium (CCM) from MDA MB-435 cells as the source of ATX. Assays were performed in 96-well plates with CCM comprising one-third of the total volume and final FS-3 and charcoal-stripped fatty acid free BSA concentrations of 1 and 30 μM in assay buffer (1 mM each $CaCl_2$ and $MgCl_2$, 5 mM KCl, 140 mM NaCl, 50 mM Tris pH 8.0). Fluorescence was read at 5 minute intervals by a Synergy2 system (BioTek, Winooski, Vt.) with excitation and emission wavelengths of 485 and 538 nm, respectively. Results are shown at 1 hour, at which point all fluorescence changes as a function of time were linear. Fluorescence readings were normalized to vehicle control after subtraction of fluorescence in the absence of CCM. Data are shown as the mean±S.D. of at least three wells. The inhibition levels are inversely related to the fluorescence change over time and concentration and converted to percentage fluorescence response to show the effectiveness of the compounds tested (low % response reflects effective inhibition). The control was LPA alone. The results of these tests for the Example compounds from above were as follows:

TABLE 2

Autotaxin Activity Reduction of Exemplified Compounds

| Example | Concentration | Time | Fluorescence (% Response) |
|---|---|---|---|
| 1 | 30 uM | 0 hour | 96.1 |
| 1 | 100 uM | 0 hour | 94.1 |
| 2 | 3 uM | 6 hours | 25.0 |
| 2 | 3 uM | 3 hours | 28.1 |
| 2 | 3 uM | 1 hour | 47.9 |
| 2 | 3 uM | 0 hour | 83.3 |
| 2 | 30 uM | 6 hours | -2.1 |
| 2 | 30 uM | 3 hours | 9.4 |
| 2 | 30 uM | 1 hour | 35.4 |
| 2 | 30 uM | 0 hour | 57.3 |
| 3 | 3 uM | 6 hours | 34.4 |
| 3 | 3 uM | 3 hours | 44.8 |
| 3 | 3 uM | 1 hour | 60.4 |
| 3 | 3 uM | 0 hour | 94.8 |
| 3 | 30 uM | 6 hours | 10.4 |
| 3 | 30 uM | 3 hours | 19.0 |
| 3 | 30 uM | 1 hour | 37.5 |
| 3 | 30 uM | 0 hour | 71.9 |
| 4 | 3 uM | 6 hours | 21.9 |
| 4 | 3 uM | 3 hours | 33.3 |
| 4 | 3 uM | 1 hour | 50.0 |
| 4 | 3 uM | 0 hour | 81.3 |
| 4 | 30 uM | 6 hours | -2.1 |
| 4 | 30 uM | 3 hours | 5.2 |
| 4 | 30 uM | 1 hour | 12.5 |
| 4 | 30 uM | 0 hour | 26.0 |
| 5 | 3 uM | 6 hours | 31.2 |
| 5 | 3 uM | 3 hours | 42.7 |
| 5 | 3 uM | 1 hour | 57.1 |
| 5 | 3 uM | 0 hour | 92.5 |
| 5 | 30 uM | 6 hours | 9.6 |
| 5 | 30 uM | 3 hours | 12.9 |
| 5 | 30 uM | 1 hour | 14.3 |
| 5 | 30 uM | 0 hour | 24.5 |
| 6 | 3 uM | 6 hours | 32.7 |
| 6 | 3 uM | 3 hours | 45.7 |
| 6 | 3 uM | 1 hour | 61.9 |
| 6 | 3 uM | 0 hour | 95.9 |
| 6 | 30 uM | 6 hours | 18.5 |
| 6 | 30 uM | 3 hours | 25.0 |
| 6 | 30 uM | 1 hour | 31.3 |
| 6 | 30 uM | 0 hour | 48.9 |
| 7 | 3 uM | 6 hours | 37.0 |
| 7 | 3 uM | 3 hours | 48.3 |
| 7 | 3 uM | 1 hour | 64.5 |
| 7 | 3 uM | 0 hour | 93.9 |
| 7 | 30 uM | 6 hours | 24.9 |
| 7 | 30 uM | 3 hours | 29.4 |
| 7 | 30 uM | 1 hour | 36.2 |
| 7 | 30 uM | 0 hour | 52.0 |
| 8 | 3 uM | 6 hours | 40.6 |
| 8 | 3 uM | 3 hours | 52.2 |
| 8 | 3 uM | 1 hour | 70.0 |
| 8 | 3 uM | 0 hour | 99.4 |
| 8 | 30 uM | 6 hours | 37.7 |
| 8 | 30 uM | 3 hours | 48.4 |
| 8 | 30 uM | 1 hour | 63.0 |
| 8 | 30 uM | 0 hour | 89.1 |
| 9 | 3 uM | 6 hours | 42.1 |
| 9 | 3 uM | 3 hours | 51.0 |
| 9 | 3 uM | 1 hour | 74.5 |
| 9 | 3 uM | 0 hour | 97.6 |
| 9 | 30 uM | 6 hours | 38.4 |
| 9 | 30 uM | 3 hours | 44.2 |
| 9 | 30 uM | 1 hour | 61.4 |
| 9 | 30 uM | 0 hour | 81.8 |
| 10 | 3 uM | 6 hours | 4.7 |
| 10 | 3 uM | 3 hours | 10.6 |
| 10 | 3 uM | 1 hour | 29.3 |
| 10 | 3 uM | 0 hour | 86.6 |
| 10 | 30 uM | 6 hours | -17.0 |
| 10 | 30 uM | 3 hours | -18.7 |
| 10 | 30 uM | 1 hour | -16.8 |
| 10 | 30 uM | 0 hour | 0.4 |
| LPA | 1 uM | 6 hours | 1.0 |
| LPA | 1 uM | 3 hours | 1.0 |

TABLE 2-continued

Autotaxin Activity Reduction of Exemplified Compounds

| Example | Concentration | Time | Fluorescence (% Response) |
|---------|---------------|------|---------------------------|
| LPA | 1 uM | 1 hour | 10.4 |
| LPA | 1 uM | 0 hour | 15.6 |

A decrease in % response upon increasing time reflects irreversible inhibition of autotaxin, and is exhibited by the majority of examples studied (eg. Example 3 at 3 uM showed a reduction from 94.8% response at hour 0 to 34.4% response at hour 6). Thus, it is evident that the inventive compounds exhibit excellent potential for autotaxin inactivation, particularly within an aqueous system, as compared with the LPA control (1 uM showed a minimal change from 15.6% response at hour 0 to 1.0% response at hour 6), at least.

There are, of course, many alternative embodiments and modifications of the present invention which are intended to be included within the spirit and scope of this invention.

What we claimed is:

1. A compound conforming to the structure of Formula (II):

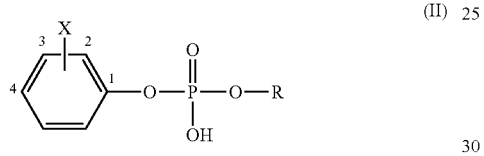

(II)

wherein R is $C_{12-18}$ alkyl or alkenyl, X is $CH_2F$ or $CHF_2$, and X is located at either position 2 or 4.

2. The compound of claim 1 wherein X is located in the 4 position and X is $CH_2F$.

3. The compound of claim 1 wherein X is located in the 2 position and X is $CH_2F$.

4. A method of reducing autotaxin activity in its ability to react with lysophosphatidyl choline to form lysophosphatidic acid, said method comprising the introduction of the compound of claim 1 within an aqueous system including an amount of autotaxin and an amount of a lysophosphatidyl choline.

5. A method of reducing autotaxin activity in its ability to react with lysophosphatidyl choline to form lysophosphatidic acid, said method comprising the introduction of the compound of claim 2 within an aqueous system including an amount of autotaxin and an amount of a lysophosphatidyl choline.

6. A method of reducing autotaxin activity in its ability to react with lysophosphatidyl choline to form lysophosphatidic acid, said method comprising the introduction of the compound of claim 3 within an aqueous system including an amount of autotaxin and an amount of a lysophosphatidyl choline.

7. A method of producing the compound of claim 1 comprising the sequential steps of:
   a) reacting phosphorus oxychloride with a $C_{12-18}$ fatty alcohol;
   b) reacting the resultant compound of step "a" with a hydroxybenzaldehyde, thereby forming a phosphodiester compound;
   c) reacting said phosphodiester compound with a cyanoethanol to form a phosphotriester compound;
   d) reacting said phosphotriester compound with Deoxofluor, wherein said reaction with Deoxofluor is optionally preceded by reducing said phosphotriester compound with sodium borohydride, thereby producing a fluorinated compound; and
   e) deprotecting the resultant fluorinated compound of step "d".

* * * * *